United States Patent
Gao et al.

(10) Patent No.: US 12,157,892 B2
(45) Date of Patent: Dec. 3, 2024

(54) DOMINANT CRISPR INVERTED-REPEAT ALLELES TO DOWN-REGULATE GENE EXPRESSION IN HETEROZYGOUS PLANTS

(71) Applicant: PIONEER HI-BRED INTERNATIONAL, INC., Johnston, IA (US)

(72) Inventors: Huirong Gao, Johnston, IA (US); Jeffrey Habben, Urbandale, IA (US); Sabrina Humbert, Johnston, IA (US); Jinrui Shi, Johnston, IA (US)

(73) Assignee: PIONEER HI-BRED INTERNATIONAL, INC., Johnston, IA (US)

( * ) Notice: Subject to any disclaimer, the term of this patent is extended or adjusted under 35 U.S.C. 154(b) by 801 days.

(21) Appl. No.: 17/151,856

(22) Filed: Jan. 19, 2021

(65) Prior Publication Data

US 2021/0222183 A1  Jul. 22, 2021

Related U.S. Application Data

(60) Provisional application No. 62/964,383, filed on Jan. 22, 2020.

(51) Int. Cl.
    *C12N 15/82* (2006.01)
(52) U.S. Cl.
    CPC ..... *C12N 15/8213* (2013.01); *C12N 15/8216* (2013.01); *C12N 2310/20* (2017.05); *C12N 2800/80* (2013.01)

(58) Field of Classification Search
    None
    See application file for complete search history.

(56) References Cited

U.S. PATENT DOCUMENTS

| | | | |
|---|---|---|---|
| 5,510,474 A * | 4/1996 | Quail et al. ........ | C12N 15/8237 435/71.1 |
| 2015/0059010 A1* | 2/2015 | Cigan et al. ....... | C12N 15/8213 800/298 |
| 2018/0371479 A1 | 12/2018 | Cigan et al. | |
| 2019/0040405 A1 | 2/2019 | Cigan et al. | |
| 2019/0311018 A1 | 10/2019 | Kendall | |
| 2022/0177900 A1 | 6/2022 | Cigan et al. | |
| 2022/0364107 A1 | 11/2022 | Gao et al. | |
| 2023/0235345 A1 | 7/2023 | Cigan et al. | |

OTHER PUBLICATIONS

Jiang & Wessler (2001) Plant Cell 13:2553-64.*

* cited by examiner

*Primary Examiner* — Russell T Boggs (57) ABSTRACT

The disclosure provides plant, plant parts, plant cells, seed and grain containing a targeted genetic modification that inserts an inverted repeat sequence into a gene. The disclosure further provides hybrid plants that contain the inverted repeat sequence in a single allele of the gene. Further provided are methods for decreasing expression of a gene encoding a polypeptide of interest in a hybrid plant by crossing a plant comprising the targeted genetic modification with a plant not comprising the genetic modification to produce a hybrid plant that contains the inverted repeat sequence in a single allele of the gene.

20 Claims, 2 Drawing Sheets

Specification includes a Sequence Listing.

DOMINANT CRISPR INVERTED-REPEAT ALLELES TO DOWN-REGULATE GENE EXPRESSION IN HETEROZYGOUS PLANTS

CROSS-REFERENCE TO RELATED APPLICATIONS

This application claims the benefit of U.S. Provisional Application No. 62/964,383 filed on Jan. 22, 2020, which is incorporated herein by reference in its entirety.

REFERENCE TO SEQUENCE LISTING SUBMITTED ELECTRONICALLY

The official copy of the sequence listing is submitted electronically via EFS-Web as an ASCII formatted sequence listing with a file named 8193-US—PSP_SequenceListing_ST25.txt created on 20 Jan. 2020 and having a size of 5.7 kilobytes and is filed concurrently with the specification. The sequence listing comprised in this ASCII formatted document is part of the specification and is herein incorporated by reference in its entirety.

FIELD

This disclosure relates to the field of molecular biology, in particular, to the use of gene editing to down-regulate gene expression in heterozygous plants.

BACKGROUND

Dominant alleles are preferred alleles over recessive alleles in the development of economically important traits in hybrid crops because only one parent needs to carry a favorable allele to produce hybrids having the desired characteristic. In this respect, mutations conferring gene overexpression in hybrid plants are usually dominant. However, mutations conferring knockouts and alleles with reduced gene expression are often recessive.

Accordingly, there is a need to develop compositions and methods for the dominant knockdown of gene expression in hybrid plants. This disclosure provides such compositions and methods.

SUMMARY

Provided herein is a plant cell comprising a targeted genetic modification in a gene encoding a polypeptide of interest, wherein the targeted genetic modification introduces an inverted repeat sequence into the gene encoding the polypeptide of interest. In certain embodiments, the genetic modification is present in only one allele of the gene encoding the polypeptide of interest. In certain embodiments, the inverted repeat sequence is operably linked to the endogenous promoter of the gene encoding the polypeptide of interest. In certain embodiments, the inverted repeat sequence is operably linked to a heterologous promoter. In certain embodiments, the plant cell comprises in operable linkage from 5' to 3', the endogenous promoter of the gene encoding the polypeptide of interest, the inverted repeat sequence, and a region of the gene encoding the polypeptide of interest comprising a nucleotide sequence that hybridizes to the inverted repeat sequence. In certain embodiments, the plant cell comprises in operable linkage from 5' to 3', the heterologous promoter, the inverted repeat sequence, and a region of the gene encoding the polypeptide of interest comprising a nucleotide sequence that hybridizes to the inverted repeat sequence. In certain embodiments, the plant cell comprises a spacer sequence between the inverted repeat sequence and the promoter. In certain embodiments the spacer is an intron sequence, such as maize ubiquitin intron 1 (SEQ ID NO: 1). In certain embodiments, the spacer comprises at least 50 nucleotides. In certain embodiments the inverted repeat sequence comprises at least 100 nucleotides. In certain embodiments, the genetic modification removes at least one exon of the gene encoding the polypeptide of interest. In certain embodiments, the gene of interest encodes a zinc finger containing protein, a kinase, a heat shock protein, a channel protein, an agronomic trait enhancing protein, an insect resistance protein, a disease resistance protein, a herbicide resistance protein, a transcription factor, a hormone biosynthesis enzyme, or a protein involved in sterility. In certain embodiments, the targeted genetic modification is introduced using a genome modification technique selected from the group comprising a polynucleotide-guided endonuclease, CRISPR-Cas endonuclease, base editing deaminases, a zinc finger nuclease, a transcription activator-like effector nuclease (TALEN), or engineered site-specific meganucleases. In certain embodiments, the plant cell is from a plant selected from the group consisting of maize, sorghum, wheat, sunflower, canola, rice, cotton, and alfalfa.

Also provided are plants comprising any of the plant cells described herein and seeds produced by the plants.

Further provided are hybrid plants, and seeds thereof, produced by crossing any of the plants described herein with a second plant. In certain embodiments, the second plant does not comprise the targeted genetic modification of the gene encoding the polypeptide of interest. In certain embodiments, the targeted genetic modification is present at only one allele of the gene encoding the polypeptide of interest. In certain embodiments, the hybrid plant is selected from the group consisting of maize, sorghum, wheat, sunflower, canola, rice, cotton, and alfalfa.

Provided is a method of producing a hybrid plant having decreased expression of a polypeptide of interest, the method comprising crossing any of the plants described herein with a second plant to generate a hybrid plant, wherein the hybrid plant comprises the inverted repeat sequence in the gene encoding the polypeptide of interest. In certain embodiments, the second plant does not comprise the inverted repeat sequence in the gene encoding the polypeptide of interest. In certain embodiments, the targeted genetic modification is present at only one allele of the gene encoding the polypeptide of interest. In certain embodiments, the hybrid plant is selected from the group consisting of maize, sorghum, wheat, sunflower, canola, rice, cotton, and alfalfa.

Further provided is a method of producing a hybrid plant having decreased expression of a polypeptide of interest, the method comprising (a) introducing in a regenerable plant cell a targeted genetic modification at a gene encoding the polypeptide of interest, wherein the targeted genetic modification introduces an inverted repeat sequence into the gene encoding the polypeptide of interest; (b) generating the plant, wherein the plant comprises the targeted genetic modification; and (c) crossing the plant of (b) with a second plant to produce a hybrid plant wherein the hybrid plant comprises at least one allele comprising the targeted genetic modification. In certain embodiments, the second plant does not comprise the targeted genetic modification. In certain embodiments, the targeted genetic modification in the hybrid plant is present at only one allele of the gene encoding the polypeptide of interest. In certain embodiments, the inverted repeat sequence is operably linked to the endogenous promoter of the gene encoding the polypeptide of interest. In certain embodiments, the inverted repeat sequence is operably linked to a heterologous promoter. In certain embodiments, the plant cell comprises in operable linkage from 5' to 3', the endogenous promoter of the gene encoding the polypeptide of interest, the inverted repeat sequence, and a region of the gene encoding the polypeptide of interest comprising a nucleotide sequence that hybridizes to the inverted repeat sequence. In certain embodiments, the plant cell comprises in operable linkage from 5' to 3', the heterologous promoter, the inverted repeat sequence, and a region of the gene encoding the polypeptide of interest comprising a nucleotide sequence that hybridizes to the inverted repeat sequence. In certain embodiments, the plant cell comprises a spacer sequence between the inverted repeat sequence and the promoter. In certain embodiments the spacer is an intron sequence, such as maize ubiquitin intron 1 (SEQ ID NO: 1). In certain embodiments, the spacer comprises at least 50 nucleotides. In certain embodiments the inverted repeat sequence comprises at least 100 nucleotides. In certain embodiments, the genetic modification removes at least one exon of the gene encoding the polypeptide of interest. In certain embodiments, the gene of interest encodes a zinc finger containing protein, a kinase, a heat shock protein, a channel protein, an agronomic trait enhancing protein, an insect resistance protein, a disease resistance protein, a herbicide resistance protein, a transcription factor, a hormone biosynthesis enzyme, or a protein involved in sterility. In certain embodiments, the targeted genetic modification is introduced using a genome modification technique selected from the group comprising a polynucleotide-guided endonuclease, CRISPR-Cas endonuclease, base editing deaminases, a zinc finger nuclease, a transcription activator-like effector nuclease (TALEN), or engineered site-specific meganucleases. In certain embodiments, the plant cell is from a plant selected from the group consisting of maize, sorghum, wheat, sunflower, canola, rice, cotton, and alfalfa.

BRIEF DESCRIPTION OF THE DRAWINGS AND THE SEQUENCE LISTING

The disclosure can be more fully understood from the following detailed description and the accompanying drawings and Sequence Listing, which form a part of this application.

The sequence descriptions and sequence listing attached hereto comply with the rules governing nucleotide and amino acid sequence disclosures in patent applications as set forth in 37 C.F.R. §§ 1.821 and 1.825. The sequence descriptions comprise the three letter codes for amino acids as defined in 37 C.F.R. §§ 1.821 and 1.825, which are incorporated herein by reference.

TABLE 1

| SEQ ID NO: | Description |
|---|---|
| 1 | Intron 1 from the maize ubiquitin gene (UBI1ZM Intron1) |
| 2 | sixth exon of RTA3 in the inverted direction |
| 3 | guide RNA ZM-RTA3-CR1 |
| 4 | guide RNA ZM-RTA3-CR2 |
| 5 | RTA3 repair template |

DETAILED DESCRIPTION

The present disclosure provides plants, plant parts, plant cells, seed, and/or grain comprising a targeted genetic modification in a gene encoding a polypeptide of interest, wherein the targeted genetic modification introduces an inverted repeat sequence into the gene encoding the polypeptide of interest. In certain embodiments, the targeted genetic modification is present on a single allele of the gene encoding the polypeptide of interest.

As used herein, "gene" includes a nucleic acid fragment that expresses a functional molecule such as, but not limited to, a specific protein coding sequence and regulatory elements, such as a promoter, an enhancer, an intron, a 5'-untranslated region (5'-UTR, also known as a leader sequence), or a 3'-untranslated region (3'-UTR).

As used herein "inverted repeat sequence" refers to a nucleotide sequence that is the reverse complement of a sequence of the gene encoding the polypeptide of interest. The length of the inverted repeat sequence is not particularly limited so long as the inverted repeat sequence can hybridize to the complementary sequence in the gene and produce a double-stranded RNA (dsRNA). In certain embodiments the inverted repeat sequence comprises at least 100 base pairs (e.g., at least 150, at least 200, at least 250, at least 300, at least 350, at least 400, at least 450, at least 500, at least 550, at least 600, at least 650, at least 700, at least 750, at least 800, at least 850, at least 900, at least 950, or at least 1000).

In certain embodiments, the targeted genetic modification results in the gene comprising, in operable linkage, a promoter, the inverted repeat sequence, and a region of the gene encoding the polypeptide that comprises a nucleotide sequence that hybridizes to the inverted repeat sequence.

In certain embodiments the inverted repeat sequence is inserted upstream of the region of the gene comprising a nucleotide sequence that hybridizes to the inverted repeat sequence. In certain embodiments, the inverted repeat is inserted downstream of the region of the gene comprising a nucleotide sequence that hybridizes to the inverted repeat sequence. In certain embodiments, the plant cell comprising the targeted genetic modification comprises in operable linkage from 5' to 3', a promoter, the inverted repeat sequence, and the region of the gene comprising a nucleotide sequence that hybridizes to the inverted repeat sequence. In certain embodiments, the plant cell comprising the targeted genetic modification comprises in operable linkage from 5' to 3', a promoter, the region of the gene comprising a nucleotide sequence that hybridizes to the inverted repeat sequence, and the inverted repeat sequence.

In certain embodiments, the inverted repeat sequence is operably linked to the endogenous (i.e., native) promoter of the gene encoding the polypeptide of interest. In certain embodiments, the inverted repeat sequence is operably linked to a heterologous promoter.

As used herein "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide that is from a species different from the species from which the polynucleotide was derived, or, if from the same/analogous species, one or both are substantially modified from their original form and/or genomic locus, or the promoter is not the native promoter for the operably linked polynucleotide.

As used herein "promoter" refers to a region of DNA upstream from the start of transcription and involved in recognition and binding of RNA polymerase and other proteins to initiate transcription. A "plant promoter" is a promoter capable of initiating transcription in plant cells. Exemplary plant promoters include, but are not limited to, those that are obtained from plants, plant viruses and bacteria which comprise genes expressed in plant cells such *Agrobacterium* or *Rhizobium*. Certain types of promoters preferentially initiate transcription in certain tissues, such as leaves, roots, seeds, fibres, xylem vessels, tracheids or sclerenchyma. Such promoters are referred to as "tissue preferred." A "cell type" specific promoter primarily drives expression in certain cell types in one or more organs, for example, vascular cells in roots or leaves. An "inducible" or "regulatable" promoter is a promoter, which is under environmental control. Examples of environmental conditions that may affect transcription by inducible promoters include anaerobic conditions or the presence of light. Another type of promoter is a developmentally regulated promoter, for example, a promoter that drives expression during pollen development. Tissue preferred, cell type specific, developmentally regulated and inducible promoters constitute the class of "non-constitutive" promoters. A "constitutive" promoter is a promoter, which is active under most environmental conditions. Constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) Nature 313:810-812); rice actin (McElroy et al. (1990) Plant Cell 2:163-171); ubiquitin (Christensen et al. (1989) Plant Mol. Biol. 12:619-632 and Christensen et al. (1992) Plant Mol. Biol. 18:675-689); pEMU (Last et al. (1991) Theor. Appl. Genet. 81:581-588); MAS (Velten et al. (1984) EMBO J. 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

In certain embodiments, the plant, plant part, plant cell, seed and/or grain comprises a first spacer sequence between the promoter and the inverted repeat sequence. The number of nucleotides and sequence of the first spacer sequence is not particularly limited and can be selected based on the desired expression level and/or outcome. In certain embodiments, the first spacer sequence comprises an intron sequence, such as, for example, intron 1 from the maize ubiquitin gene (SEQ ID NO: 1).

In certain embodiments, the plant, plant part, plant cell, seed and/or grain comprises a second spacer sequence between the inverted repeat sequence and the region of the gene comprising a nucleotide sequence that hybridizes to the inverted repeat sequence. The number of nucleotides and sequence of the second spacer sequence is not particularly limited and can be selected based on the desired expression level and/or outcome. In certain embodiments, the second spacer sequence comprises at least 50 nucleotides (e.g., at least 100, at least 150, at least 200, at least 250, at least 300, at least 350, at least 400, at least 450, at least 500, at least 550, at least 600, at least 650, at least 700, at least 750, at least 800, at least 850, at least 900, at least 950, or at least 1000).

In certain embodiments, the targeted genetic modification removes at least one exon of the gene encoding the polypeptide of interest.

The terms "polypeptide of interest" "gene of interest" and the like are synonymous and generally refer to any polypeptide for which decreased expression is desired.

The polypeptide of interest for use in the methods and compositions described herein is not particularly limited and is reflective of the commercial markets and interests of those involved in the development of the crop. Crops and markets of interest change, and as developing nations open world markets, new crops and technologies will emerge also. In addition, as our understanding of agronomic characteristics and traits such as yield and heterosis increase, the choice of genes for transformation may change accordingly.

General categories of polypeptide of interest include, but are not limited to, those polypeptides involved in information, such as zinc fingers, those involved in communication, such as kinases, those involved in transport, such as porins, and those involved in housekeeping, such as heat shock proteins. More specific categories, for example, include, but are not limited to, polypeptides encoding important traits for agronomics (e.g., yield enhancing, drought resistance, nitrogen use efficiency, maturity, flowering time, senescence, stature, plant architecture, leaf angle and morphology), insect resistance, disease resistance, herbicide resistance, sterility, grain or seed characteristics, and commercial products.

Polypeptides of interest include, generally, those involved in oil, starch, carbohydrate, or nutrient metabolism as well as those affecting seed size, plant development, plant growth regulation, and yield improvement. Plant development and growth regulation also refer to the development and growth regulation of various parts of a plant, such as the flower, seed, root, leaf and shoot.

Other commercially desirable traits are genes and proteins conferring cold, heat, salt, and drought resistance.

Disease and/or insect resistance polypeptides may encode resistance to pests that have great yield drag such as for example, Northern Corn Leaf Blight, head smut, anthracnose, soybean mosaic virus, soybean cyst nematode, rootknot nematode, brown leaf spot, Downy mildew, purple seed stain, seed decay and seedling diseases caused commonly by the fungi-*Pythium* sp., *Phytophthora* sp., *Rhizoctonia* sp., *Diaporthe* sp. Bacterial blight caused by the bacterium *Pseudomonas syringae* pv. Glycinea. Polypeptides conferring insect resistance include, for example, *Bacillus thuringiensis* toxic protein genes (U.S. Pat. Nos. 5,366,892; 5,747,450; 5,737,514; 5,723,756; 5,593,881; and Geiser et al (1986) Gene 48:109); lectins (Van Damme et al. (1994) Plant Mol. Biol. 24:825); and the like.

Herbicide resistance traits may include genes coding for resistance to herbicides that act to inhibit the action of acetolactate synthase (ALS), in particular the sulfonylurea-type herbicides (e.g., the acetolactate synthase ALS gene containing mutations leading to such resistance, in particular the S4 and/or HRA mutations). The ALS-gene mutants encode resistance to the herbicide chlorsulfuron. Glyphosate acetyl transferase (GAT) is an N-acetyltransferase from *Bacillus licheniformis* that was optimized by gene shuffling for acetylation of the broad-spectrum herbicide, glyphosate, forming the basis of a novel mechanism of glyphosate tolerance in transgenic plants (Castle et al. (2004) Science 304, 1151-1154).

Polypeptides involved in plant growth and development have been identified in plants. One such gene, which is involved in cytokinin biosynthesis, is isopentenyl transferase (IPT). Cytokinin plays a critical role in plant growth and development by stimulating cell division and cell differentiation (Sun et al. (2003), Plant Physiol. 131:167-176).

In certain embodiments, the polypeptide of interest is a polypeptide that is native to the plant, plant cells, plant parts, seeds, and/or grain (e.g., endogenous gene). In certain embodiments, the polypeptide of interest is a polypeptide that has been inserted into the plant, plant cells, plant parts, seeds, and/or grain, such as, for example, a polypeptide encoded by a gene under the control of a heterologous promoter.

In certain embodiments, the inverted repeat sequence is designed to decrease expression of the polypeptide of interest and at least one homologous gene (e.g., genes of the same family or paralogous disease genes). In certain embodiments, the at least one homologous gene encodes a polypeptide comprising an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to the polypeptide of interest.

Examples of plant species of the compositions and methods described herein include, but are not limited to, maize (*Zea mays*), *Brassica* sp. (e.g., *B. napus*, *B. rapa*, *B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (Carthamus tinctorius), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (Citrus spp.), cocoa (*Theobroma cacao*), tea (*Camellia sinensis*), banana (Musa spp.), avocado (*Persea americana*), fig (*Ficus* casica), guava (*Psidium guajava*), mango (*Mangifera indica*), olive (*Olea europaea*), *papaya* (*Carica papaya*), cashew (*Anacardium occidentale*), macadamia (Macadamia *integrifolia*), almond (*Prunus* amygdalus), sugar beets (*Beta vulgaris*), sugarcane (*Saccharum* spp.), oats, barley, vegetables, ornamentals, conifers, turf grasses (including cool seasonal grasses and warm seasonal grasses).

Vegetables include, for example, tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus* rosasanensis), roses (Rosa spp.), tulips (*Tulipa* spp.), daffodils (*Narcissus* spp.), petunias (*Petunia hybrida*), carnation (*Dianthus* caryophyllus), poinsettia (*Euphorbia pulcherrima*), and *chrysanthemum*.

Conifers that may be employed in practicing that which is disclosed include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow cedar (*Chamaecyparis nootkatensis*), and Poplar and *Eucalyptus*. In specific embodiments, plants of the present disclosure are crop plants (for example, corn, alfalfa, sunflower, *Brassica*, soybean, cotton, safflower, peanut, sorghum, wheat, millet, tobacco, etc.). In other embodiments, corn and soybean plants are optimal, and in yet other embodiments corn plants are optimal.

Other plants of interest include, for example, grain plants that provide seeds of interest, oil-seed plants, and leguminous plants. Seeds of interest include, for example, grain seeds, such as corn, wheat, barley, rice, sorghum, rye, etc. Oil-seed plants include, for example, cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea.

In certain embodiments, the plant is selected from the group consisting of maize, sorghum, wheat, sunflower, canola, rice, cotton, and alfalfa.

Also provided are hybrid plants produced by crossing a plant comprising any of the targeted genetic modifications described herein with a second plant. In certain embodiments, the second plant does not comprise the targeted genetic modification. In certain embodiments, the targeted genetic modification is not present on all alleles of the gene encoding the polypeptide of interest in the hybrid plant. In certain embodiments, the targeted modification is present on only one allele of the gene encoding the polypeptide of interest in the hybrid plant. In certain embodiments, the hybrid plant is selected from the group consisting of maize, sorghum, wheat, sunflower, canola, rice, cotton, and alfalfa.

Methods

Provided herein are methods of producing a hybrid plant having decreased expression of a polypeptide of interest, comprising crossing a plant comprising a targeted genetic modification that introduces an inverted repeat sequence into a gene encoding a polypeptide of interest with a second plant to generate a hybrid plant, wherein the hybrid plant comprises the inverted repeat sequence in the gene encoding the polypeptide of interest. In certain embodiments, the method comprises: (a) introducing in a regenerable plant cell the targeted genetic modification at the gene encoding the polypeptide of interest; (b) generating the plant, wherein the plant comprises the targeted genetic modification; and (c) crossing the plant of (b) with a second plant to produce a hybrid plant wherein the hybrid plant comprises the genetic modification in at least one allele of the gene encoding the polypeptide of interest.

In certain embodiments, the second plant does not comprise the inverted repeat sequence in the gene encoding the polypeptide of interest. In certain embodiments, the hybrid plant comprises the targeted genetic modification on only one allele of the gene encoding the polypeptide of interest.

The targeted genetic modification of the methods described herein can be any genetic modification described herein, such that the targeted genetic modification results in any of the plants described herein. Additionally, the plant for use in the methods described herein may be any plant described herein. In certain embodiments, the plant is selected from the group consisting of maize, sorghum, wheat, sunflower, canola, rice, cotton, and alfalfa.

Various methods can be used to introduce the targeted genetic modification at the gene encoding the polypeptide of interest into the plant, plant part, plant cell, seed, and/or grain. In certain embodiments the targeted genetic modification is through a genome modification technique selected from the group consisting of a polynucleotide-guided endonuclease, CRISPR-Cas endonucleases, base editing deaminases, zinc finger nuclease, a transcription activator-like effector nuclease (TALEN), engineered site-specific meganuclease, or Argonaute.

In some embodiments, the genome modification may be facilitated through the induction of a double-stranded break (DSB) or single-strand break, in a defined position in the genome near the desired alteration. DSBs can be induced using any DSB-inducing agent available, including, but not limited to, TALENs, meganucleases, zinc finger nucleases, Cas9-gRNA systems (based on bacterial CRISPR-Cas systems), guided cpf1 endonuclease systems, and the like. In some embodiments, the introduction of a DSB can be combined with the introduction of a polynucleotide modification template.

A polynucleotide modification template can be introduced into a cell by any method known in the art, such as, but not limited to, transient introduction methods, transfection, electroporation, microinjection, particle mediated delivery, topical application, whiskers mediated delivery, delivery via cell-penetrating peptides, or mesoporous silica nanoparticle (MSN)-mediated direct delivery.

The polynucleotide modification template can be introduced into a cell as a single stranded polynucleotide molecule, a double stranded polynucleotide molecule, or as part of a circular DNA (vector DNA). The polynucleotide modification template can also be tethered to the guide RNA and/or the Cas endonuclease. Tethered DNAs can allow for co-localizing target and template DNA, useful in genome editing and targeted genome regulation, and can also be useful in targeting post-mitotic cells where function of endogenous HR machinery is expected to be highly diminished (Mali et al. 2013 Nature Methods Vol. 10:957-963.) The polynucleotide modification template may be present transiently in the cell or it can be introduced via a viral replicon.

A "modified nucleotide" or "edited nucleotide" refers to a nucleotide sequence of interest that comprises at least one alteration when compared to its non-modified nucleotide sequence. Such "alterations" include, for example: (i) replacement of at least one nucleotide, (ii) a deletion of at least one nucleotide, (iii) an insertion of at least one nucleotide, or (iv) any combination of (i)-(iii).

The term "polynucleotide modification template" includes a polynucleotide that comprises at least one nucleotide modification when compared to the nucleotide sequence to be edited. A nucleotide modification can be at least one nucleotide substitution, addition or deletion. Optionally, the polynucleotide modification template can further comprise homologous nucleotide sequences flanking the at least one nucleotide modification, wherein the flanking homologous nucleotide sequences provide sufficient homology to the desired nucleotide sequence to be edited.

The process for editing a genomic sequence combining DSB and modification templates generally comprises: providing to a host cell, a DSB-inducing agent, or a nucleic acid encoding a DSB-inducing agent, that recognizes a target sequence in the chromosomal sequence and is able to induce a DSB in the genomic sequence, and at least one polynucleotide modification template comprising at least one nucleotide alteration when compared to the nucleotide sequence to be edited. The polynucleotide modification template can further comprise nucleotide sequences flanking the at least one nucleotide alteration, in which the flanking sequences are substantially homologous to the chromosomal region flanking the DSB.

The endonuclease can be provided to a cell by any method known in the art, for example, but not limited to, transient introduction methods, transfection, microinjection, and/or topical application or indirectly via recombination constructs. The endonuclease can be provided as a protein or as a guided polynucleotide complex directly to a cell or indirectly via recombination constructs. The endonuclease can be introduced into a cell transiently or can be incorporated into the genome of the host cell using any method known in the art. In the case of a CRISPR-Cas system, uptake of the endonuclease and/or the guided polynucleotide into the cell can be facilitated with a Cell Penetrating Peptide (CPP) as described in WO2016073433 published May 12, 2016.

In addition to modification by a double strand break technology, modification of one or more bases without such double strand break are achieved using base editing technology, see e.g., Gaudelli et al., (2017) Programmable base editing of A*T to G*C in genomic DNA without DNA cleavage. Nature 551 (7681): 464-471; Komor et al., (2016) Programmable editing of a target base in genomic DNA without double-stranded DNA cleavage, Nature 533 (7603): 420-4.

These fusions contain dCas9 or Cas9 nickase and a suitable deaminase, and they can convert e.g., cytosine to uracil without inducing double-strand break of the target DNA. Uracil is then converted to thymine through DNA replication or repair. Improved base editors that have targeting flexibility and specificity are used to edit endogenous locus to create target variations and improve grain yield. Similarly, adenine base editors enable adenine to inosine change, which is then converted to guanine through repair or replication. Thus, targeted base changes i.e., C•G to T•A conversion and A•T to G•C conversion at one more locations made using appropriate site-specific base editors.

In an embodiment, base editing is a genome editing method that enables direct conversion of one base pair to another at a target genomic locus without requiring double-stranded DNA breaks (DSBs), homology-directed repair (HDR) processes, or external donor DNA templates. In an embodiment, base editors include (i) a catalytically impaired CRISPR-Cas9 mutant that are mutated such that one of their nuclease domains cannot make DSBs; (ii) a single-strand-specific cytidine/adenine deaminase that converts C to U or A to G within an appropriate nucleotide window in the single-stranded DNA bubble created by Cas9; (iii) a uracil glycosylase inhibitor (UGI) that impedes uracil excision and downstream processes that decrease base editing efficiency and product purity; and (iv) nickase activity to cleave the non-edited DNA strand, followed by cellular DNA repair processes to replace the G-containing DNA strand.

As used herein, a "genomic region" is a segment of a chromosome in the genome of a cell that is present on either side of the target site or, alternatively, also comprises a portion of the target site. The genomic region can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800. 5-2900, 5-3000, 5-3100 or more bases such that the genomic region has sufficient homology to undergo homologous recombination with the corresponding region of homology.

TAL effector nucleases (TALEN) are a class of sequence-specific nucleases that can be used to make double-strand breaks at specific target sequences in the genome of a plant or other organism. (Miller et al. (2011) Nature Biotechnology 29:143-148).

Endonucleases are enzymes that cleave the phosphodiester bond within a polynucleotide chain. Endonucleases include restriction endonucleases, which cleave DNA at specific sites without damaging the bases, and meganucleases, also known as homing endonucleases (HEases), which like restriction endonucleases, bind and cut at a specific recognition site, however the recognition sites for meganucleases are typically longer, about 18 bp or more (patent application PCT/US12/30061, filed on Mar. 22, 2012). Meganucleases have been classified into four families based on conserved sequence motifs, the families are the LAGLIDADG, GIY-YIG, H—N—H, and His-Cys box families. These motifs participate in the coordination of metal ions and hydrolysis of phosphodiester bonds. HEases are notable for their long recognition sites, and for tolerating some sequence polymorphisms in their DNA substrates. The naming convention for meganuclease is similar to the convention for other restriction endonuclease. Meganucleases are also characterized by prefix F—, I—, or Pl– for enzymes encoded by free-standing ORFs, introns, and inteins, respectively. One step in the recombination process involves polynucleotide cleavage at or near the recognition site. The cleaving activity can be used to produce a double-strand break. For reviews of site-specific recombinases and their recognition sites, see, Sauer (1994) Curr Op Biotechnol 5:521-7; and Sadowski (1993) FASEB 7:760-7. In some examples the recombinase is from the Integrase or Resolvase families.

Zinc finger nucleases (ZFNs) are engineered double-strand break inducing agents comprised of a zinc finger DNA binding domain and a double-strand-break-inducing agent domain. Recognition site specificity is conferred by the zinc finger domain, which typically comprising two, three, or four zinc fingers, for example having a C2H2 structure, however other zinc finger structures are known and have been engineered. Zinc finger domains are amenable for designing polypeptides which specifically bind a selected polynucleotide recognition sequence. ZFNs include an engineered DNA-binding zinc finger domain linked to a non-specific endonuclease domain, for example nuclease domain from a Type IIs endonuclease such as FokI. Additional functionalities can be fused to the zinc-finger binding domain, including transcriptional activator domains, transcription repressor domains, and methylases. In some examples, dimerization of nuclease domain is required for cleavage activity. Each zinc finger recognizes three consecutive base pairs in the target DNA. For example, a 3 finger domain recognized a sequence of 9 contiguous nucleotides, with a dimerization requirement of the nuclease, two sets of zinc finger triplets are used to bind an 18 nucleotide recognition sequence.

Genome editing using DSB-inducing agents, such as Cas9-gRNA complexes, has been described, for example in U.S. Patent Application 2015-0082478 A1, published on Mar. 19, 2015, WO2015/026886 A1, published on Feb. 26, 2015, WO2016007347, published on Jan. 14, 2016, and WO201625131, published on Feb. 18, 2016, all of which are incorporated by reference herein.

The term "Cas gene" herein refers to a gene that is generally coupled, associated or close to, or in the vicinity of flanking CRISPR loci in bacterial systems. The terms "Cas gene", "CRISPR-associated (Cas) gene" are used interchangeably herein. The term "Cas endonuclease" herein refers to a protein encoded by a Cas gene. A Cas endonuclease herein, when in complex with a suitable polynucleotide component, is capable of recognizing, binding to, and optionally nicking or cleaving all or part of a specific DNA target sequence. A Cas endonuclease described herein comprises one or more nuclease domains. Cas endonucleases of the disclosure includes those having a HNH or HNH-like nuclease domain and/or a RuvC or RuvC-like nuclease domain. A Cas endonuclease of the disclosure includes a Cas9 protein, a Cpf1 protein, a C2c1 protein, a C2c2 protein, a C2c3 protein, Cas3, Cas 5, Cas7, Cas8, Cas10, or complexes of these.

As used herein, the terms "guide polynucleotide/Cas endonuclease complex", "guide polynucleotide/Cas endonuclease system", "guide polynucleotide/Cas complex", "guide polynucleotide/Cas system", "guided Cas system" are used interchangeably herein and refer to at least one guide polynucleotide and at least one Cas endonuclease that are capable of forming a complex, wherein said guide polynucleotide/Cas endonuclease complex can direct the Cas endonuclease to a DNA target site, enabling the Cas endonuclease to recognize, bind to, and optionally nick or cleave (introduce a single or double strand break) the DNA target site. A guide polynucleotide/Cas endonuclease complex herein can comprise Cas protein(s) and suitable polynucleotide component(s) of any of the four known CRISPR systems (Horvath and Barrangou, 2010, Science 327:167-170) such as a type I, II, or III CRISPR system. A Cas endonuclease unwinds the DNA duplex at the target sequence and optionally cleaves at least one DNA strand, as mediated by recognition of the target sequence by a polynucleotide (such as, but not limited to, a crRNA or guide RNA) that is in complex with the Cas protein. Such recognition and cutting of a target sequence by a Cas endonuclease typically occurs if the correct protospacer-adjacent motif (PAM) is located at or adjacent to the 3' end of the DNA target sequence. Alternatively, a Cas protein herein may lack DNA cleavage or nicking activity but can still specifically bind to a DNA target sequence when complexed with a suitable RNA component. (See also U.S. Patent Application 2015-0082478 A1, published on Mar. 19, 2015 and US 2015-0059010 A1, published on Feb. 26, 2015, both are hereby incorporated in its entirety by reference).

A guide polynucleotide/Cas endonuclease complex can cleave one or both strands of a DNA target sequence. A guide polynucleotide/Cas endonuclease complex that can cleave both strands of a DNA target sequence typically comprise a Cas protein that has all of its endonuclease domains in a functional state (e.g., wild type endonuclease domains or variants thereof retaining some or all activity in each endonuclease domain). Non-limiting examples of Cas9 nickases suitable for use herein are disclosed in U.S. Patent Appl. Publ. No. 2014/0189896, which is incorporated herein by reference.

Other Cas endonuclease systems have been described in PCT patent applications PCT/US16/32073, filed May 12, 2016 and PCT/US16/32028 filed May 12, 2016, both applications incorporated herein by reference.

"Cas9" (formerly referred to as Cas5, Csn1, or Csx12) herein refers to a Cas endonuclease of a type II CRISPR system that forms a complex with a crNucleotide and a tracrNucleotide, or with a single guide polynucleotide, for specifically recognizing and cleaving all or part of a DNA target sequence. Cas9 protein comprises a RuvC nuclease domain and an HNH (H—N—H) nuclease domain, each of which can cleave a single DNA strand at a target sequence (the concerted action of both domains leads to DNA double-strand cleavage, whereas activity of one domain leads to a nick). In general, the RuvC domain comprises subdomains I, II and III, where domain I is located near the N-terminus of Cas9 and subdomains II and III are located in the middle of the protein, flanking the HNH domain (Hsu et al, Cell 157:1262-1278). A type II CRISPR system includes a DNA cleavage system utilizing a Cas9 endonuclease in complex with at least one polynucleotide component. For example, a Cas9 can be in complex with a CRISPR RNA (crRNA) and a trans-activating CRISPR RNA (tracrRNA). In another example, a Cas9 can be in complex with a single guide RNA.

Any guided endonuclease can be used in the methods disclosed herein. Such endonucleases include, but are not limited to, Cas9 and Cpf1 endonucleases. Many endonucleases have been described to date that can recognize specific PAM sequences (see for example—Jinek et al. (2012) Science 337 p 816-821, PCT patent applications PCT/US16/32073, filed May 12, 2016 and PCT/US16/32028 filed May 12, 2016 and Zetsche B et al. 2015. Cell 163, 1013) and cleave the target DNA at a specific position. It is understood that based on the methods and embodiments described herein utilizing a guided Cas system one can now tailor these methods such that they can utilize any guided endonuclease system.

The guide polynucleotide can also be a single molecule (also referred to as single guide polynucleotide) comprising a crNucleotide sequence linked to a tracrNucleotide sequence. The single guide polynucleotide comprises a first nucleotide sequence domain (referred to as Variable Targeting domain or VT domain) that can hybridize to a nucleotide sequence in a target DNA and a Cas endonuclease recognition domain (CER domain), that interacts with a Cas endonuclease polypeptide. By "domain" it is meant a contiguous stretch of nucleotides that can be RNA, DNA, and/or RNA-DNA-combination sequence. The VT domain and/or the CER domain of a single guide polynucleotide can comprise a RNA sequence, a DNA sequence, or a RNA-DNA-combination sequence. The single guide polynucleotide being comprised of sequences from the crNucleotide and the tracrNucleotide may be referred to as "single guide RNA" (when composed of a contiguous stretch of RNA nucleotides) or "single guide DNA" (when composed of a contiguous stretch of DNA nucleotides) or "single guide RNA-DNA" (when composed of a combination of RNA and DNA nucleotides). The single guide polynucleotide can form a complex with a Cas endonuclease, wherein said guide polynucleotide/Cas endonuclease complex (also referred to as a guide polynucleotide/Cas endonuclease system) can direct the Cas endonuclease to a genomic target site, enabling the Cas endonuclease to recognize, bind to, and optionally nick or cleave (introduce a single or double strand break) the target site. (See also U.S. Patent Application 2015-0082478 A1, published on Mar. 19, 2015 and US 2015-0059010 A1, published on Feb. 26, 2015, both are hereby incorporated in its entirety by reference.)

The term "variable targeting domain" or "VT domain" is used interchangeably herein and includes a nucleotide sequence that can hybridize (is complementary) to one strand (nucleotide sequence) of a double strand DNA target site. In some embodiments, the variable targeting domain comprises a contiguous stretch of 12 to 30 nucleotides. The variable targeting domain can be composed of a DNA sequence, a RNA sequence, a modified DNA sequence, a modified RNA sequence, or any combination thereof.

The terms "single guide RNA" and "sgRNA" are used interchangeably herein and relate to a synthetic fusion of two RNA molecules, a crRNA (CRISPR RNA) comprising a variable targeting domain (linked to a tracr mate sequence that hybridizes to a tracrRNA), fused to a tracrRNA (trans-activating CRISPR RNA). The single guide RNA can comprise a crRNA or crRNA fragment and a tracrRNA or tracrRNA fragment of the type II CRISPR/Cas system that can form a complex with a type II Cas endonuclease, wherein said guide RNA/Cas endonuclease complex can direct the Cas endonuclease to a DNA target site, enabling the Cas endonuclease to recognize, bind to, and optionally nick or cleave (introduce a single or double strand break) the DNA target site.

The terms "guide RNA/Cas endonuclease complex", "guide RNA/Cas endonuclease system", "guide RNA/Cas complex", "guide RNA/Cas system", "gRNA/Cas complex", "gRNA/Cas system", "RNA-guided endonuclease", "RGEN" are used interchangeably herein and refer to at least one RNA component and at least one Cas endonuclease that are capable of forming a complex, wherein said guide RNA/Cas endonuclease complex can direct the Cas endonuclease to a DNA target site, enabling the Cas endonuclease to recognize, bind to, and optionally nick or cleave (introduce a single or double strand break) the DNA target site. A guide RNA/Cas endonuclease complex herein can comprise Cas protein(s) and suitable RNA component(s) of any of the four known CRISPR systems (Horvath and Barrangou, 2010, Science 327:167-170) such as a type I, II, or III CRISPR system. A guide RNA/Cas endonuclease complex can comprise a Type II Cas9 endonuclease and at least one RNA component (e.g., a crRNA and tracrRNA, or a gRNA). (See also U.S. Patent Application 2015-0082478 A1, published on Mar. 19, 2015 and US 2015-0059010 A1, published on Feb. 26, 2015, both are hereby incorporated in its entirety by reference).

In certain embodiments, the guide polynucleotide is a guide RNA. The guide polynucleotide may also be present in a recombinant DNA construct.

The guide polynucleotide can be introduced into a cell transiently, as single stranded polynucleotide or a double stranded polynucleotide, using any method known in the art such as, but not limited to, particle bombardment, *Agrobacterium* transformation or topical applications. The guide polynucleotide can also be introduced indirectly into a cell by introducing a recombinant DNA molecule (via methods such as, but not limited to, particle bombardment or *Agrobacterium* transformation) comprising a heterologous nucleic acid fragment encoding a guide polynucleotide, operably linked to a specific promoter that is capable of transcribing the guide RNA in said cell. The specific promoter can be, but is not limited to, a RNA polymerase III promoter, which allow for transcription of RNA with precisely defined, unmodified, 5'- and 3'-ends (DiCarlo et al., Nucleic Acids Res. 41:4336-4343; Ma et al., Mol. Ther. Nucleic Acids 3: e161) as described in WO2016025131, published on Feb. 18, 2016, incorporated herein in its entirety by reference.

The terms "target site", "target sequence", "target site sequence, "target DNA", "target locus", "genomic target site", "genomic target sequence", "genomic target locus" and "protospacer", are used interchangeably herein and refer to a polynucleotide sequence such as, but not limited to, a nucleotide sequence on a chromosome, episome, or any other DNA molecule in the genome (including chromosomal, choloroplastic, mitochondrial DNA, plasmid DNA) of a cell, at which a guide polynucleotide/Cas endonuclease complex can recognize, bind to, and optionally nick or cleave. The target site can be an endogenous site in the genome of a cell, or alternatively, the target site can be heterologous to the cell and thereby not be naturally occurring in the genome of the cell, or the target site can be found in a heterologous genomic location compared to where it occurs in nature. As used herein, terms "endogenous target sequence" and "native target sequence" are used interchangeable herein to refer to a target sequence that is endogenous or native to the genome of a cell and is at the endogenous or native position of that target sequence in the genome of the cell. Cells include, but are not limited to, human, non-human, animal, bacterial, fungal, insect, yeast, non-conventional yeast, and plant cells as well as plants and seeds produced by the methods described herein. An "artificial target site" or "artificial target sequence" are used interchangeably herein and refer to a target sequence that has been introduced into the genome of a cell. Such an artificial target sequence can be identical in sequence to an endogenous or native target sequence in the genome of a cell but be located in a different position (i.e., a non-endogenous or non-native position) in the genome of a cell.

An "altered target site", "altered target sequence", "modified target site", "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii).

Methods for "modifying a target site" and "altering a target site" are used interchangeably herein and refer to methods for producing an altered target site.

The length of the target DNA sequence (target site) can vary, and includes, for example, target sites that are at least 12, 13, 14, 15, 16, 17, 18, 19, 20, 21, 22, 23, 24, 25, 26, 27, 28, 29, 30 or more nucleotides in length. It is further possible that the target site can be palindromic, that is, the sequence on one strand reads the same in the opposite direction on the complementary strand. The nick/cleavage site can be within the target sequence or the nick/cleavage site could be outside of the target sequence. In another variation, the cleavage could occur at nucleotide positions immediately opposite each other to produce a blunt end cut or, in other Cases, the incisions could be staggered to produce single-stranded overhangs, also called "sticky ends", which can be either 5' overhangs, or 3' overhangs. Active variants of genomic target sites can also be used. Such active variants can comprise at least 65%, 70%, 75%, 80%, 85%, 90%, 91%, 92%, 93%, 94%, 95%, 96%, 97%, 98%, 99% or more sequence identity to the given target site, wherein the active variants retain biological activity and hence are capable of being recognized and cleaved by an Cas endonuclease. Assays to measure the single or double-strand break of a target site by an endonuclease are known in the art and generally measure the overall activity and specificity of the agent on DNA substrates containing recognition sites.

A "protospacer adjacent motif" (PAM) herein refers to a short nucleotide sequence adjacent to a target sequence (protospacer) that is recognized (targeted) by a guide polynucleotide/Cas endonuclease system described herein. The Cas endonuclease may not successfully recognize a target DNA sequence if the target DNA sequence is not followed by a PAM sequence. The sequence and length of a PAM herein can differ depending on the Cas protein or Cas protein complex used. The PAM sequence can be of any length but is typically 1, 2, 3, 4, 5, 6, 7, 8, 9, 10, 11, 12, 13, 14, 15, 16, 17, 18, 19 or 20 nucleotides long.

The terms "targeting", "gene targeting" and "DNA targeting" are used interchangeably herein. DNA targeting herein may be the specific introduction of a knock-out, edit, or knock-in at a particular DNA sequence, such as in a chromosome or plasmid of a cell. In general, DNA targeting can be performed herein by cleaving one or both strands at a specific DNA sequence in a cell with an endonuclease associated with a suitable polynucleotide component. Such DNA cleavage, if a double-strand break (DSB), can prompt NHEJ or HDR processes which can lead to modifications at the target site.

A targeting method herein can be performed in such a way that two or more DNA target sites are targeted in the method, for example. Such a method can optionally be characterized as a multiplex method. Two, three, four, five, six, seven, eight, nine, ten, or more target sites can be targeted at the same time in certain embodiments. A multiplex method is typically performed by a targeting method herein in which multiple different RNA components are provided, each designed to guide an guidepolynucleotide/Cas endonuclease complex to a unique DNA target site.

The guide polynucleotide/Cas endonuclease system can be used in combination with a co-delivered polynucleotide modification template to allow for editing (modification) of a genomic nucleotide sequence of interest. (See also U.S. patent application 2015-0082478 A1, published on Mar. 19, 2015 and WO2015/026886 A1, published on Feb. 26, 2015, both are hereby incorporated in its entirety by reference.)

Various methods and compositions can be employed to obtain a cell or organism having a polynucleotide of interest inserted in a target site for a Cas endonuclease. Such methods can employ homologous recombination to provide integration of the polynucleotide of Interest at the target site. In one method provided, a polynucleotide of interest is provided to the organism cell in a donor DNA construct. As used herein, "donor DNA" is a DNA construct that comprises a polynucleotide of Interest to be inserted into the target site of a Cas endonuclease. The donor DNA construct further comprises a first and a second region of homology that flank the polynucleotide of Interest. The first and second regions of homology of the donor DNA share homology to a first and a second genomic region, respectively, present in or flanking the target site of the cell or organism genome. By "homology" is meant DNA sequences that are similar. For example, a "region of homology to a genomic region" that is found on the donor DNA is a region of DNA that has a similar sequence to a given "genomic region" in the cell or organism genome. A region of homology can be of any length that is sufficient to promote homologous recombination at the cleaved target site. For example, the region of homology can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800, 5-2900, 5-3000, 5-3100 or more bases in length such that the region of homology has sufficient homology to undergo homologous recombination with the corresponding genomic region. "Sufficient homology" indicates that two polynucleotide sequences have sufficient structural similarity to act as substrates for a homologous recombination reaction. The structural similarity includes overall length of each polynucleotide fragment, as well as the sequence similarity of the polynucleotides. Sequence similarity can be described by the percent sequence identity over the whole length of the sequences, and/or by conserved regions comprising localized similarities such as contiguous nucleotides having 100% sequence identity, and percent sequence identity over a portion of the length of the sequences.

The amount of sequence identity shared by a target and a donor polynucleotide can vary and includes total lengths and/or regions having unit integral values in the ranges of about 1-20 bp, 20-50 bp, 50-100 bp, 75-150 bp, 100-250 bp, 150-300 bp, 200-400 bp, 250-500 bp, 300-600 bp, 350-750 bp, 400-800 bp, 450-900 bp, 500-1000 bp, 600-1250 bp, 700-1500 bp, 800-1750 bp, 900-2000 bp, 1-2.5 kb, 1.5-3 kb, 2-4 kb, 2.5-5 kb, 3-6 kb, 3.5-7 kb, 4-8 kb, 5-10 kb, or up to and including the total length of the target site. These ranges include every integer within the range, for example, the range of 1-20 bp includes 1, 2, 3, 4, 5, 6, 7, 8, 9, 10, 11, 12, 13, 14, 15, 16, 17, 18, 19 and 20 bps. The amount of homology can also be described by percent sequence identity over the full aligned length of the two polynucleotides which includes percent sequence identity of about at least 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. Sufficient homology includes any combination of polynucleotide length, global percent sequence identity, and optionally conserved regions of contiguous nucleotides or local percent sequence identity, for example sufficient homology can be described as a region of 75-150 bp having at least 80% sequence identity to a region of the target locus. Sufficient homology can also be described by the predicted ability of two polynucleotides to specifically hybridize under high stringency conditions, see, for example, Sambrook et al., (1989) Molecular Cloning: A Laboratory Manual, (Cold Spring Harbor Laboratory Press, NY); Current Protocols in Molecular Biology, Ausubel et al., Eds (1994) Current Protocols, (Greene Publishing Associates, Inc. and John Wiley & Sons, Inc.); and, Tijssen (1993) Laboratory Techniques in Biochemistry and Molecular Biology—Hybridization with Nucleic Acid Probes, (Elsevier, New York).

The structural similarity between a given genomic region and the corresponding region of homology found on the donor DNA can be any degree of sequence identity that allows for homologous recombination to occur. For example, the amount of homology or sequence identity shared by the "region of homology" of the donor DNA and the "genomic region" of the organism genome can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, such that the sequences undergo homologous recombination The region of homology on the donor DNA can have homology to any sequence flanking the target site. While in some embodiments the regions of homology share significant sequence homology to the genomic sequence immediately flanking the target site, it is recognized that the regions of homology can be designed to have sufficient homology to regions that may be further 5' or 3' to the target site. In still other embodiments, the regions of homology can also have homology with a fragment of the target site along with downstream genomic regions. In one embodiment, the first region of homology further comprises a first fragment of the target site and the second region of homology comprises a second fragment of the target site, wherein the first and second fragments are dissimilar.

As used herein, "homologous recombination" includes the exchange of DNA fragments between two DNA molecules at the sites of homology.

Further uses for guide RNA/Cas endonuclease systems have been described (See U.S. Patent Application 2015-0082478 A1, published on Mar. 19, 2015, WO2015/026886 A1, published on Feb. 26, 2015, US 2015-0059010 A1, published on Feb. 26, 2015, U.S. application 62/023,246, filed on Jul. 7, 2014, and U.S. application 62/036,652, filed on Aug. 13, 2014, all of which are incorporated by reference herein) and include but are not limited to modifying or replacing nucleotide sequences of interest (such as a regulatory elements), insertion of polynucleotides of interest, gene knock-out, gene-knock in, modification of splicing sites and/or introducing alternate splicing sites, modifications of nucleotide sequences encoding a protein of interest, amino acid and/or protein fusions, and gene silencing by expressing an inverted repeat into a gene of interest.

Methods for transforming dicots, primarily by use of *Agrobacterium tumefaciens*, and obtaining transgenic plants have been published, among others, for cotton (U.S. Pat. Nos. 5,004,863, 5,159,135); soybean (U.S. Pat. Nos. 5,569, 834, 5,416,011); *Brassica* (U.S. Pat. No. 5,463,174); peanut (Cheng et al., Plant Cell Rep. 15:653 657 (1996), McKently et al., Plant Cell Rep. 14:699 703 (1995)); *papaya* (Ling et al., Bio/technology 9:752 758 (1991)); and pea (Grant et al., Plant Cell Rep. 15:254 258 (1995)). For a review of other commonly used methods of plant transformation see Newell, C. A., Mol. Biotechnol. 16:53 65 (2000). One of these methods of transformation uses *Agrobacterium rhizogenes* (Tepfler, M. and Casse-Delbart, F., Microbiol. Sci. 4:24 28 (1987)). Transformation of soybeans using direct delivery of DNA has been published using PEG fusion (PCT Publication No. WO 92/17598), electroporation (Chowrira et al., Mol. Biotechnol. 3:17 23 (1995); Christou et al., Proc. Natl. Acad. Sci. U.S.A. 84:3962 3966 (1987)), microinjection, or particle bombardment (McCabe et al., Biotechnology 6:923-926 (1988); Christou et al., Plant Physiol. 87:671 674 (1988)).

There are a variety of methods for the regeneration of plants from plant tissues. The particular method of regeneration will depend on the starting plant tissue and the particular plant species to be regenerated. The regeneration, development and cultivation of plants from single plant protoplast transformants or from various transformed explants is well known in the art (Weissbach and Weissbach, Eds.; In Methods for Plant Molecular Biology; Academic Press, Inc.: San Diego, CA, 1988). This regeneration and growth process typically includes the steps of selection of transformed cells, culturing those individualized cells through the usual stages of embryonic development or through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present disclosure containing a desired polypeptide is cultivated using methods well known to one skilled in the art.

The following are examples of specific embodiments of some aspects of the invention. The examples are offered for illustrative purposes only and are not intended to limit the scope of the invention in any way.

Terms used in the claims and specification are defined as set forth below unless otherwise specified. It must be noted that, as used in the specification and the appended claims, the singular forms "a," "an" and "the" include plural referents unless the context clearly dictates otherwise. All cited patents and publications referred to in this application are herein incorporated by reference in their entirety, for all purposes, to the same extent as if each were individually and specifically incorporated by reference.

The following are examples of specific embodiments of some aspects of the invention. The examples are offered for illustrative purposes only and are not intended to limit the scope of the invention in any way. Efforts have been made to ensure accuracy with respect to numbers used (e.g., amounts, temperatures, etc.), but some experimental error and deviation should, of course, be allowed for.

EXAMPLE 1

This example demonstrates the introduction of an inverted repeat in a gene encoding a polypeptide of interest to decrease expression of the gene.

This example was designed to test whether down-regulating the expression of a gene of interest can be achieved in a hybrid (e.g., heterozygous) plant comprising one allele of the gene of interest having an inserted inverted repeat sequence.

Figure 1:
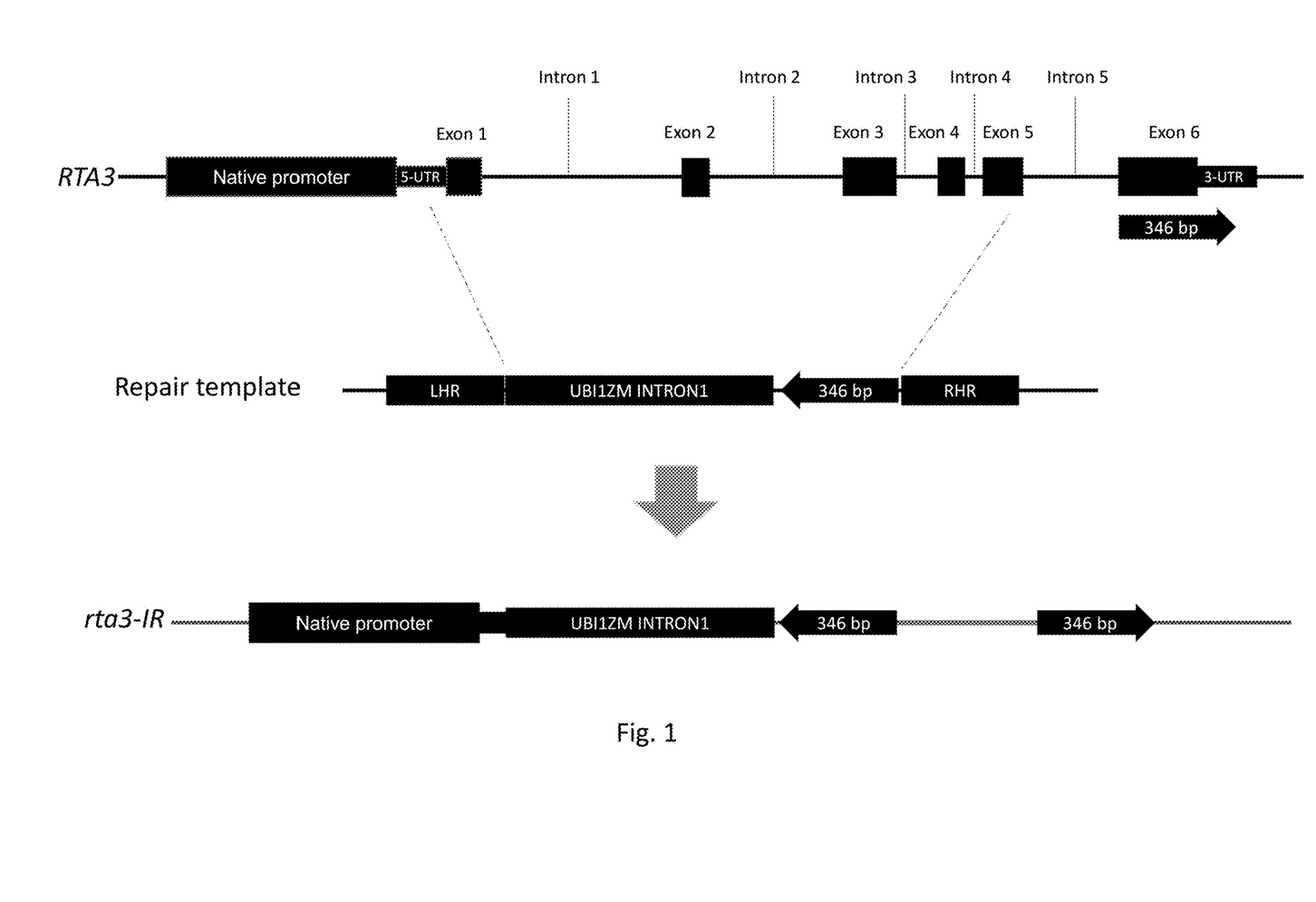
FIG. 1 is a schematic providing the strategy for introducing the inverted repeat sequence into the gene RTA3 gene.

An inverted repeat-containing allele of the maize RTA3 gene, comprising the RTA3 native promoter, the maize ubiquitin intron1 (SEQ ID NO 1), a 346-bp fragment of the sixth exon of RTA3 in the inverted direction (SEQ ID NO 2), the fifth intron and the sixth exon of RTA3, was generated by using genome editing via CRISPR-Cas9 (FIG. 1). The CRISPR-Cas9 genome-editing reagents include DNA plasmids containing *S. pyogenes* Cas9, two guide RNA ZM-RTA3-CR1 and ZM-RTA3-CR2 (SEQ ID NOs: 3 and 4, respectively) and a repair template (SEQ ID NO 5). The two gRNA were designed to direct CRISPR-Cas9 cutting in the first and fifth exon of the maize RTA3 gene, respectively. The repair template consists of the maize ubiquitin intron 1 (SEQ ID NO 1) and the 346-bp fragment of RTA3 Exon 6 in the inverted direction (SEQ ID NO 2), flanked by two DNA sequences of 400-bp homologous to the genomic sequences immediately adjacent to the CRISPR-Cas9 target sequences. Under the direction of guide RNAs, CRISPR-Cas9 cuts in the first and fifth exons of RTA3, removing a fragment of 3.2-kb genomic sequence (i.e. RTA3 Exon 1 to Exon 5) and leaving two free chromosomal ends. Homology-directed repair of the double-strand DNA breaks using the repair template (SEQ ID NO 5) inserts the maize ubiquitin intron 1 and the inverted repeat sequence, generating an inverted repeat allele for the RTA3 gene.

Maize immature embryos were co-bombarded with the plasmid DNA. Regenerated plantlets were screened using junction PCR assays for deletion and insertion events. Positive T0 plants were crossed to recurrent parent (the wild-type of the same inbred line as initially transformed) to produce BC0 seeds. The sequence of modified RTA3 alleles was confirmed by PCR amplification of the entire region in T0 followed by sequencing, and the integrity of the RTA3 locus was further verified by Southern-by-Sequencing analysis of BC0 plants. The DNA vectors that were bombarded may have been incorporated into chromosome(s). Therefore, PCR assays were used to screen BC0 plants to select null segregants that contain the RTA3 inverted repeat allele, but are free from genome-editing reagent plasmids. Selected clean BC0 plants were backcrossed to the recurrent parent again to generate BC1 seeds.

The RTA3 inverted repeat allele (rta3-IR) was designed to reduce the transcript abundance of the wildtype RTA3 allele in a heterozygous plant (rta3-IR RTA3). To determine this effect, the transcript expression level of the RTA3 gene in heterozygous rta3-IR RTA3 plants were compared to that in a heterozygous plant carrying a CRISPR-Cas9 induced knockout allele of RTA3 (rta3-KO) and a wildtype RTA3 allele. The rta3-OK allele was generated by deleting the first exon to fifth exon of the RTA3 gene. The transcript abundance was measured by quantitative reverse transcription PCR (RT-qPCR) with gene-specific primers derived from the first and the second exon of RTA3. The relative expression levels in homozygous wildtype plants (RTA3 RTA3) were set as 100%. Seeds were planted in greenhouse. Root samples were taken from V3 seedlings and leaf samples were taken from the third leaves of V3 seedlings and the 12th leaves of V14 plants.

Figure 2:
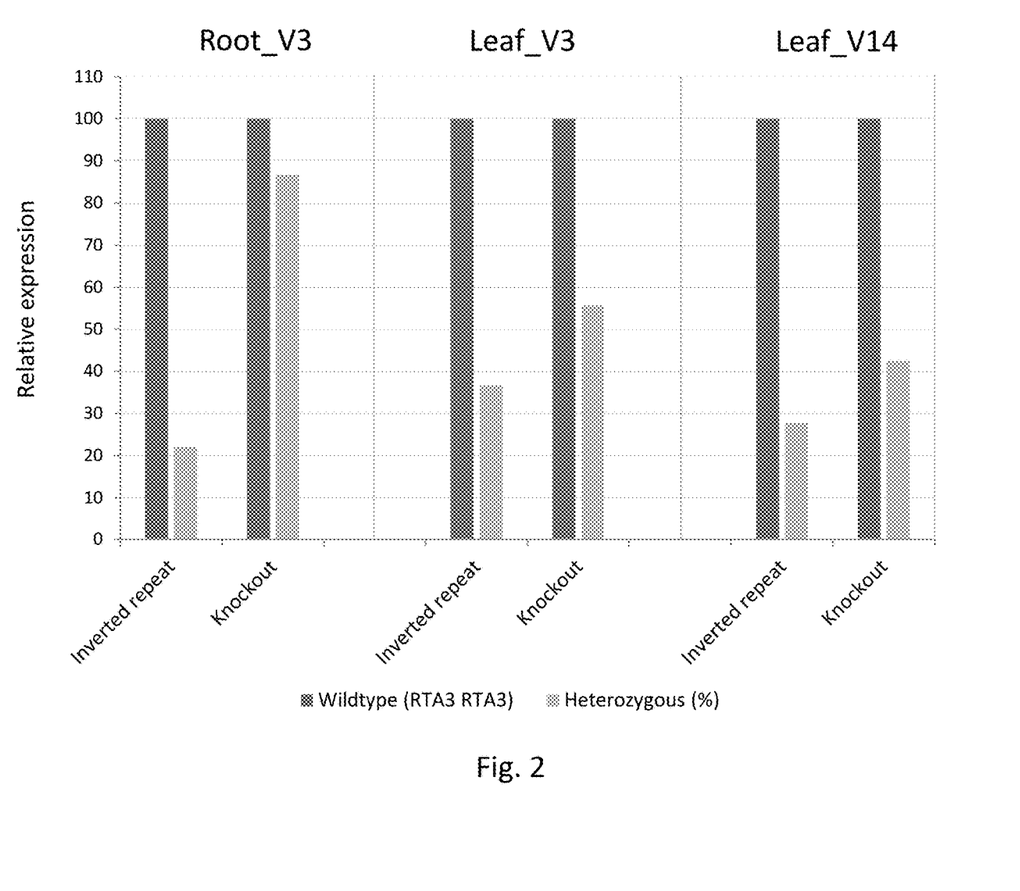
FIG. 2 provides experimental results showing the expression of RTA3 in maize root at v3 and leaf tissue at v3 and v14 in wild-type maize plants, plants comprising the inverted repeat in an allele of the RTA3 gene, and plants comprising a knockout of an allele of the RTA3 gene.

As shown in FIG. 2, heterozygous (hybrid) plants comprising the inverted repeat have lower RTA3 expression than the heterozygous plants containing the knockout allele.

These results demonstrate that the insertion of an inverted repeat at a single allele of a gene of interest can significantly decrease expression of a gene encoding a polypeptide of interest.

All publications and patent applications in this specification are indicative of the level of ordinary skill in the art to which this invention pertains. All publications and patent applications are herein incorporated by reference to the same extent as if each individual publication or patent application was specifically and individually indicated by reference.

Unless defined otherwise, all technical and scientific terms used herein have the same meaning as commonly understood by one of ordinary skill in the art to which this invention belongs. Unless mentioned otherwise, the techniques employed or contemplated herein are standard methodologies well known to one of ordinary skill in the art. The materials, methods and examples are illustrative only and not limiting.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

Units, prefixes and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

We claim:

1. A plant cell comprising a targeted genetic modification in a gene encoding a polypeptide of interest, the targeted genetic modification removing at least one exon in the gene encoding the polypeptide of interest and introducing an inverted repeat nucleotide sequence and a first spacer nucleotide sequence into the gene encoding the polypeptide of interest, so that the plant cell comprises in operable linkage from 5' to 3' a promoter operably linked to the gene encoding the polypeptide of interest, the spacer sequence, the inverted repeat sequence, and a region of the gene encoding the polypeptide of interest, the inverted repeat nucleotide sequence comprising a reverse complement of at least 100 nucleotides of an exon of the gene encoding the polypeptide of interest and the spacer sequence comprising at least 100 consecutive nucleotides of SEQ ID NO: 1.

2. The plant cell of claim 1, wherein the targeted genetic modification is present in only one allele of the gene encoding the polypeptide of interest.

3. The plant cell of claim 1, wherein the promoter comprises the endogenous promoter of the gene encoding the polypeptide of interest.

4. The plant cell of claim 1, wherein the region of the gene encoding the polypeptide of interest comprises at least 100 nucleotides of an exon of the gene encoding the polypeptide of interest that hybridizes to the inverted repeat sequence.

5. The plant cell of claim 1, wherein the first spacer nucleotide sequence comprises SEQ ID NO: 1.

6. The plant cell of claim 1, wherein the plant cell comprises a second spacer nucleotide sequence comprising at least 50 nucleotides between the inverted repeat nucleotide sequence and the region of the gene encoding the polypeptide of interest.

7. The plant cell of claim 1, wherein the inverted repeat sequence comprises the reverse complement of at least 100 consecutive nucleotides of the exon of the gene encoding the polypeptide of interest.

8. The plant cell of claim 1, wherein the gene of interest encodes a zinc finger containing protein, a kinase, a heat shock protein, a channel protein, an agronomic trait enhancing protein, an insect resistance protein, a disease resistance protein, a herbicide resistance protein, a transcription factor, a hormone biosynthesis enzyme or a protein involved in sterility.

9. The plant cell of claim 1, wherein the plant cell is from a plant selected from the group consisting of maize, sorghum, wheat, sunflower, canola, rice, cotton, and alfalfa.

10. A plant comprising the plant cell of claim 1.

11. A seed produced by the plant of claim 10, wherein the seed comprises the targeted genetic modification.

12. A hybrid plant produced by crossing the plant of claim 10 with a second plant.

13. The hybrid plant of claim 12, wherein the second plant does not comprise the targeted genetic modification of the gene encoding the polypeptide of interest.

14. A seed produced by the hybrid plant of claim 13.

15. A method of producing a hybrid plant having decreased expression of a polypeptide of interest, the method comprising crossing the plant of claim 10 with a second plant to generate a hybrid plant, wherein the hybrid plant comprises the inverted repeat nucleotide sequence in the gene encoding the polypeptide of interest.

16. The method of claim 15, wherein the second plant does not comprise the targeted genetic modification.

17. The method of claim 15, wherein the targeted genetic modification in the hybrid plant is present at only one allele of the gene encoding the polypeptide of interest.

18. The method of claim 15, wherein the gene of interest encodes a zinc finger containing protein, a kinase, a heat shock protein, a channel protein, an agronomic trait enhancing protein, an insect resistance protein, a disease resistance protein, a herbicide resistance protein, a transcription factor, a hormone biosynthesis enzyme, or a protein involved in sterility.

19. The method of claim 15, wherein the targeted genetic modification is introduced using an enzyme selected from the group comprising a polynucleotide-guided endonuclease, CRISPR-Cas endonuclease, base editing deaminases, a zinc finger nuclease, a transcription activator-like effector nuclease (TALEN), or engineered site-specific meganucleases.

20. The method of claim 15, wherein the plant is selected from the group consisting of maize, sorghum, wheat, sunflower, canola, rice, cotton, and alfalfa.

* * * * *

SEQUENCE LISTING

<160> NUMBER OF SEQ ID NOS: 5

<210> SEQ ID NO 1
<211> LENGTH: 1092
<212> TYPE: DNA
<213> ORGANISM: zea mays

<400> SEQUENCE: 1

| | | | | | |
|---|---|---|---|---|---|
| tccccaacct | cgtgttgttc | ggagcgcaca | cacacacaac | cagatctccc | ccaaatccac | 60 |
| ccgtcggcac | ctccgcttca | aggtacgccg | ctcgtcctcc | ccccccccc | tctctacctt | 120 |
| ctctagatcg | gcgttccggt | ccaatggtta | gggcccggta | gttctacttc | tgttcatgtt | 180 |
| tgtgttagat | ccgtgtttgt | gttagatccg | tgctgctagc | gttcgtacac | ggatgcgacc | 240 |
| tgtacgtcag | acacgttctg | attgctaact | tgccagtgtt | tctctttggg | gaatcctggg | 300 |
| atggctctag | ccgttccgca | gacgggatcg | atttcatgat | ttttttttgtt | tcgttgcata | 360 |
| gggtttggtt | tgccctttc | ctttatttca | atatatgccg | tgcacttgtt | tgtcgggtca | 420 |
| tcttttcatg | ctttttttttg | tcttggttgt | gatgatgtgg | tctggttggg | cggtcgttct | 480 |
| agatcggagt | agaattctgt | ttcaaactac | ctggtggatt | tattaatttt | ggatctgtat | 540 |
| gtgtgtgcca | tacatattca | tagttacgaa | ttgaagatga | tggatggaaa | tatcgatcta | 600 |
| ggataggtat | acatgttgat | gcgggtttta | ctgatgcata | tacagagatg | cttttttgttc | 660 |
| gcttggttgt | gatgatgtgg | tgtggttggg | cggtcgttca | ttcgttctag | atcggagtag | 720 |
| aatactgttt | caaactacct | ggtgtattta | ttaattttgg | aactgtatgt | gtgtgtcata | 780 |
| catcttcata | gttacgagtt | taagatggat | ggaaatatcg | atctaggata | ggtatacatg | 840 |
| ttgatgtggg | ttttactgat | gcatatacat | gatggcatat | gcagcatcta | ttcatatgct | 900 |
| ctaaccttga | gtacctatct | attataataa | acaagtatgt | tttataatta | ttttgatctt | 960 |
| gatatacttg | gatgatggca | tatgcagcag | ctatatgtgg | atttttttag | ccctgccttc | 1020 |
| atacgctatt | tatttgcttg | gtactgtttc | ttttgtcgat | gctcaccctg | ttgtttggtg | 1080 |
| ttacttctgc | ag | | | | | 1092 |

<210> SEQ ID NO 2
<211> LENGTH: 345
<212> TYPE: DNA
<213> ORGANISM: Zea mays

<400> SEQUENCE: 2

| | | | | | |
|---|---|---|---|---|---|
| ttacctatcg | gcaagagctt | caggatctga | gaatgtcgtt | gacgcggtct | cggaatacat | 60 |
| tgcatccccg | acgatcctct | tctgcaggtt | ctccaggcta | gcaacacggt | gcagagaagc | 120 |
| tggcttggtc | tgaaaaactg | ctgcgtttgg | gatgatccca | ctgttttcaa | gtggcgcctg | 180 |
| gaggaaatgc | ttcacgctgt | cttcaatggc | ggcagaagca | gaagcagaag | ctgcatcaga | 240 |
| tggacatgat | gacaggggcg | cgctgctcgt | gggcttctca | aaagcggtcg | gtagcatgag | 300 |
| ggtgatccca | gttagcctcc | tgacagcttc | ctaggctatg | ttcac | | 345 |

<210> SEQ ID NO 3
<211> LENGTH: 18
<212> TYPE: DNA
<213> ORGANISM: Artificial Sequence
<220> FEATURE:
<223> OTHER INFORMATION: guide RNA

<400> SEQUENCE: 3
gagcagcctg agcaatgt                                                18

<210> SEQ ID NO 4
<211> LENGTH: 19
<212> TYPE: DNA
<213> ORGANISM: Artificial Sequence
<220> FEATURE:
<223> OTHER INFORMATION: guide RNA

<400> SEQUENCE: 4
gcattctcag acgttaacc								19

<210> SEQ ID NO 5
<211> LENGTH: 2238
<212> TYPE: DNA
<213> ORGANISM: Artificial Sequence
<220> FEATURE:
<223> OTHER INFORMATION: repair template

<400> SEQUENCE: 5

| | | | | | |
|---|---|---|---|---|---|
| atatatttag | aatctaaatt | tagttaaagt | agagaacctt | aggattatct | ctattatata |   60 |
| agcatacata | tctatacttt | taacattaag | gggtgtttga | tttataggga | ctaattttta |  120 |
| gttccatcat | tttattttat | tttagtacct | aaattactaa | atatagaaac | tgtaattcta |  180 |
| ttttagtttt | tatatttatg | aatttatgac | taaaatagaa | taaaataaat | ttagccccat |  240 |
| agaaaccaaa | cacactataa | tacaggataa | tgaaatgaga | aacaaaagca | agggtgtttc |  300 |
| ccggaaaaga | ccaacagtgt | cgccactcgc | cacagagcgc | tccatcaaca | cgaccgccgg |  360 |
| tataaacgca | gccccctcc  | ggcctccacc | aaggccaaca | tccccaacct | cgtgttgttc |  420 |
| ggagcgcaca | cacacacaac | cagatctccc | ccaaatccac | ccgtcggcac | ctccgcttca |  480 |
| aggtacgccg | ctcgtcctcc | cccccccccc | tctctacctt | ctctagatcg | gcgttccggt |  540 |
| ccaatggtta | gggcccggta | gttctacttc | tgttcatgtt | tgtgttagat | ccgtgtttgt |  600 |
| gttagatccg | tgctgctagc | gttcgtacac | ggatgcgacc | tgtacgtcag | acacgttctg |  660 |
| attgctaact | tgccagtgtt | tctctttggg | gaatcctggg | atggctctag | ccgttccgca |  720 |
| gacgggatcg | atttcatgat | tttttttgtt | tcgttgcata | gggtttggtt | tgcccttttc |  780 |
| ctttatttca | atatatgccg | tgcacttgtt | tgtcgggtca | tcttttcatg | cttttttttg |  840 |
| tcttggttgt | gatgatgtgg | tctggttggg | cggtcgttct | agatcggagt | agaattctgt |  900 |
| ttcaaactac | ctggtggatt | tattaatttt | ggatctgtat | gtgtgtgcca | tacatattca |  960 |
| tagttacgaa | ttgaagatga | tggatggaaa | tatcgatcta | ggataggtat | acatgttgat | 1020 |
| gcgggtttta | ctgatgcata | tacagagatg | cttttttgttc | gcttggttgt | gatgatgtgg | 1080 |
| tgtggttggg | cggtcgttca | ttcgttctag | atcggagtag | aatactgttt | caaactacct | 1140 |
| ggtgtattta | ttaattttgg | aactgtatgt | gtgtgtcata | catcttcata | gttacgagtt | 1200 |
| taagatggat | ggaaatatcg | atctaggata | ggtatacatg | ttgatgtggg | ttttactgat | 1260 |
| gcatatacat | gatggcatat | gcagcatcta | ttcatatgct | ctaaccttga | gtacctatct | 1320 |
| attataataa | acaagtatgt | tttataatta | ttttgatctt | gatatacttg | gatgatggca | 1380 |
| tatgcagcag | ctatatgtgg | attttttttag | ccctgccttc | atacgctatt | tatttgcttg | 1440 |
| gtactgtttc | ttttgtcgat | gctcaccctg | ttgtttggtg | ttacttctgc | aggttaccta | 1500 |
| tcggcaagag | cttcaggatc | tgagaatgtc | gttgacgcgg | tctcggaata | cattgcatcc | 1560 |
| ccgacgatcc | tcttctgcag | gttctccagg | ctagcaacac | ggtgcagaga | agctggcttg | 1620 |
| gtctgaaaaa | ctgctgcgtt | tgggatgatc | ccactgtttt | caagtggcgc | ctggaggaaa | 1680 |

-continued

```
tgcttcacgc tgtcttcaat ggcggcagaa gcagaagcag aagctgcatc agatggacat    1740
gatgacaggg gcgcgctgct cgtgggcttc tcaaaagcgg tcggtagcat gagggtgatc    1800
ccagttagcc tcctgacagc ttcctaggct atgttcacta acgtctgaga atgcatcttt    1860
gctgaagcga ctggctgata tgactcagaa atacaaggac gcttccgttg acaataaaaa    1920
tctaacagtt gatgttgaga ctatgaggag aaaggttcgt tcgtcttgaa tgcatcacag    1980 accttttttct tctttttttt gttgtacgag aactcttaac tgcatccatt tatcgatcat    2040
aacattttta ctgggctctg tgtatactca ccgtaatcaa cgtttacatc tctctagatg    2100
gctgcaaagg gcagtgaaag taatatgatt gttcatagtt cttattttag aacctgcaag    2160
ttcagtttta gtttctaatg gtttttaact gcacacaaaa ggtatggcag cattttcatt    2220
tgattttctg aaattctg                                                   2238
```